US012690778B2

(12) United States Patent
Ludwin et al.

(10) Patent No.: US 12,690,778 B2
(45) Date of Patent: Jul. 28, 2026

(54) SCALING IMPEDANCE LOCATION MEASUREMENTS OF A BALLOON CATHETER

(71) Applicant: Biosense Webster (Israel) Ltd., Yokneam (IL)

(72) Inventors: Doron Moshe Ludwin, Haifa (IL); Avigdor Rosenberg, Kiryat Tivon (IL); Aharon Turgeman, Zichron Ya'acov (IL); Michael Maydel, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 857 days.

(21) Appl. No.: 15/985,149

(22) Filed: May 21, 2018

(65) Prior Publication Data

US 2019/0350489 A1 Nov. 21, 2019

(51) Int. Cl.
| | |
|---|---|
| *A61B 5/0538* | (2021.01) |
| *A61B 5/00* | (2006.01) |
| *A61M 25/10* | (2013.01) |
| *A61B 17/00* | (2006.01) |
| *A61B 18/00* | (2006.01) |

(52) U.S. Cl.
CPC .......... *A61B 5/0538* (2013.01); *A61B 5/6853* (2013.01); *A61B 2017/00026* (2013.01); *A61B 2017/00039* (2013.01); *A61B 2018/0022* (2013.01); *A61M 25/10* (2013.01)

(58) Field of Classification Search
CPC .......... A61B 5/6853; A61B 2017/3486; A61B 2018/0022; A61F 2/2433; A61M 3/0295; A61M 25/10
See application file for complete search history.

(56) References Cited

U.S. PATENT DOCUMENTS

| | | | |
|---|---|---|---|
| 5,391,199 | A | 2/1995 | Ben-Haim |
| 5,553,611 | A | 9/1996 | Budd et al. |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |

(Continued)

FOREIGN PATENT DOCUMENTS

| | | |
|---|---|---|
| CN | 101828915 A | 9/2010 |
| CN | 104023663 A | 9/2014 |

(Continued)

OTHER PUBLICATIONS

European Search Report dated Sep. 3, 2019, Application No. EP 19 17 5457.

(Continued)

*Primary Examiner* — Linda C Dvorak
*Assistant Examiner* — Christine A Dedoulis
(74) *Attorney, Agent, or Firm* — FBT Gibbons LLP

(57) ABSTRACT

A method includes, in a processor, receiving position signals that are indicative of positions of (i) multiple electrodes disposed on an inflatable balloon fitted at a distal end of a catheter, and (ii) first and second electrodes fitted on a shaft of the catheter, on either side of the balloon. The positions of the multiple electrodes disposed on the balloon are calculated based on the received position signals and based on a known distance between the first and second electrodes.

19 Claims, 3 Drawing Sheets

(56) References Cited

U.S. PATENT DOCUMENTS

| | | | |
|---|---|---|---|
| 6,690,963 B2 | 2/2004 | Ben-Haim et al. | |
| 6,892,091 B1 | 5/2005 | Ben-Haim et al. | |
| 6,973,339 B2 | 12/2005 | Govari | |
| 7,756,576 B2 | 7/2010 | Levin | |
| 7,848,787 B2 | 12/2010 | Osadchy | |
| 7,869,865 B2 | 1/2011 | Govari et al. | |
| 9,867,556 B2 | 1/2018 | Balachandran et al. | |
| 2002/0055674 A1 | 5/2002 | Ben-Haim et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2004/0176664 A1 | 9/2004 | Iddan | |
| 2006/0178587 A1 | 8/2006 | Khoury | |
| 2007/0016007 A1 | 1/2007 | Govari et al. | |
| 2008/0234564 A1 | 9/2008 | Beatty et al. | |
| 2009/0253976 A1 | 10/2009 | Harlev et al. | |
| 2009/0253985 A1 | 10/2009 | Shachar et al. | |
| 2009/0262109 A1 | 10/2009 | Markowitz et al. | |
| 2009/0262980 A1* | 10/2009 | Markowitz | A61B 5/0422 |
| | | | 382/103 |
| 2010/0168557 A1 | 7/2010 | Deno et al. | |
| 2012/0302869 A1 | 11/2012 | Koyrakh et al. | |
| 2013/0274582 A1* | 10/2013 | Afonso | A61B 5/066 |
| | | | 600/374 |
| 2014/0095105 A1* | 4/2014 | Koyrakh | G01C 21/00 |
| | | | 702/152 |
| 2015/0141982 A1* | 5/2015 | Lee | A61B 5/6858 |
| | | | 606/41 |
| 2017/0347896 A1 | 12/2017 | Keyes et al. | |
| 2017/0367615 A1 | 12/2017 | Markovitz et al. | |

FOREIGN PATENT DOCUMENTS

| | | | |
|---|---|---|---|
| JP | 2015-100706 A | 6/2015 | |
| JP | 2016-521180 A | 7/2016 | |
| JP | 2016-147018 A | 8/2016 | |
| WO | WO 1996/05768 | 2/1996 | |
| WO | WO 2016/040394 | 9/2015 | |
| WO | WO 2016/205807 A1 | 12/2016 | |

OTHER PUBLICATIONS

JPO Notification of Reasons for Refusal mailed Mar. 28, 2023 issued in JP Patent Application No. 2019-094328, 8 pages (English translation).
EPO EESR dated Sep. 11, 2019, issued in EP Patent Application No. 19175457.1, 9 pages.
EPO Examination Report dated Sep. 24, 2020, issued in EP Patent Application No. 19175457.1, 5 pages.
Chinese First Office Action and Search Report dated Sep. 28, 2023, for Application No. 201910423715.0, 10 pages.
Chinese Second Office Action and Search Report dated Mar. 20, 2024, for Application No. 201910423715.0, 10 pages.
Meyer, Hu. "An integrated capacitive position sensor." *IEEE transactions on instrumentation and measurement 45.2* (1996): 521-525.

* cited by examiner

SCALING IMPEDANCE LOCATION MEASUREMENTS OF A BALLOON CATHETER

FIELD OF THE INVENTION

The present invention relates generally to tracking a probe position within a living body, and specifically to improving electrical-based position measurements.

BACKGROUND OF THE INVENTION

Tracking the position of intrabody probes, such as insertion tubes, catheters and implants, is required for many medical procedures. For example, U.S. Patent Application Publication 2014/0095105 describes an algorithm to correct and/or scale an electrical current-based coordinate system that can include the determination of one or more global transformation or interpolation functions and/or one or more local transformation functions. The global and local transformation functions can be determined by calculating a global metric tensor and a number of local metric tensors. The metric tensors can be calculated based on pre-determined and measured distances between closely-spaced sensors on a catheter.

As another example, U.S. Patent Application Publication 2007/0016007 describes position sensing system that includes a probe adapted to be introduced into a body cavity of a subject. The probe includes a magnetic field transducer and at least one probe electrodes. A control unit is configured to measure position coordinates of the probe using the magnetic field transducer. The control unit also measures an impedance between the at least one probe electrodes and one or more points on a body surface of the subject. Using the measured position coordinates, the control unit calibrates the measured impedance.

U.S. Patent Application Publication 2012/0302869 describes a system and method for navigating a medical device within a body. The system includes an electronic control unit (ECU) configured to determine operating positions for electrical and magnetic position sensors on the medical device within corresponding first and second coordinate systems. The first and second coordinate systems are defined by an electric field based positioning system and a magnetic field based positioning system, respectively. The magnetic position sensor is disposed proximate the electrical position sensor. The ECU is further configured to apply a mapping function correlating the operating positions which generates a mapped position for the magnetic position sensor in the first coordinate system responsive to the operating position of the magnetic position sensor in the second coordinate system. The ECU determines an adjusted operating position for the electrical position sensor in the first coordinate system responsive to the mapped position of the magnetic position sensor.

SUMMARY OF THE INVENTION

An embodiment of the present invention provides a method including, in a processor, receiving position signals that are indicative of positions of (i) multiple electrodes disposed on an inflatable balloon fitted at a distal end of a catheter, and (ii) first and second electrodes fitted on a shaft of the catheter, on either side of the balloon. The positions of the multiple electrodes disposed on the balloon are calculated based on the received position signals and based on a known distance between the first and second electrodes.

In some embodiments, calculating the positions of the electrodes includes receiving, from a magnetic sensor disposed at the distal end of the shaft, one or more direction signals indicative of a direction of the distal end, and calculating the positions of the electrodes based on (i) the position signals (ii) the direction signals, and (iii) the known distance between the first and second electrodes.

In some embodiments, calculating the positions of the electrodes includes estimating the positions of the two sensing electrodes based on the position signals. A direction of the catheter distal end is estimated based on the direction signals. Displacements of the first and second electrodes, which would bring the first and second electrodes into correct positions along the direction of the catheter distal end, are calculated based on the known distance between the first and second electrodes. The positions of the electrodes are scaled based on the calculated displacements.

In some embodiments, calculating the positions of the electrodes includes calculating in parallel the positions of the two sensing electrodes, and the direction of the catheter distal, and the displacements of the first and second electrodes.

There is additionally provided, in accordance with an embodiment of the present invention, a system, including a balloon catheter and a processor. The balloon catheter includes a shaft, an inflatable balloon fitted at a distal end of the shaft, multiple electrodes disposed on the inflatable balloon, and first and second electrodes fitted on the shaft on either side of the balloon. The processor is configured to receive signals that are indicative of positions of the multiple electrodes disposed on the inflatable balloon and the first and second electrodes fitted on the shaft, and to calculate the positions of the multiple electrodes disposed on the balloon, based on the received signals and on a known distance between the first and second electrodes.

There is also provided, in accordance with an embodiment of the present invention, a balloon catheter, including a shaft, an inflatable balloon, and first and second electrodes. The inflatable balloon is fitted at a distal end of the shaft. The first and second electrodes are fitted on the shaft, on either side of the balloon, and are configured to transmit electrical signals indicative of respective positions of the first and second electrodes.

The present invention will be more fully understood from the following detailed description of the embodiments thereof, taken together with the drawings in which:

DETAILED DESCRIPTION OF EMBODIMENTS

Overview

Figure 1:
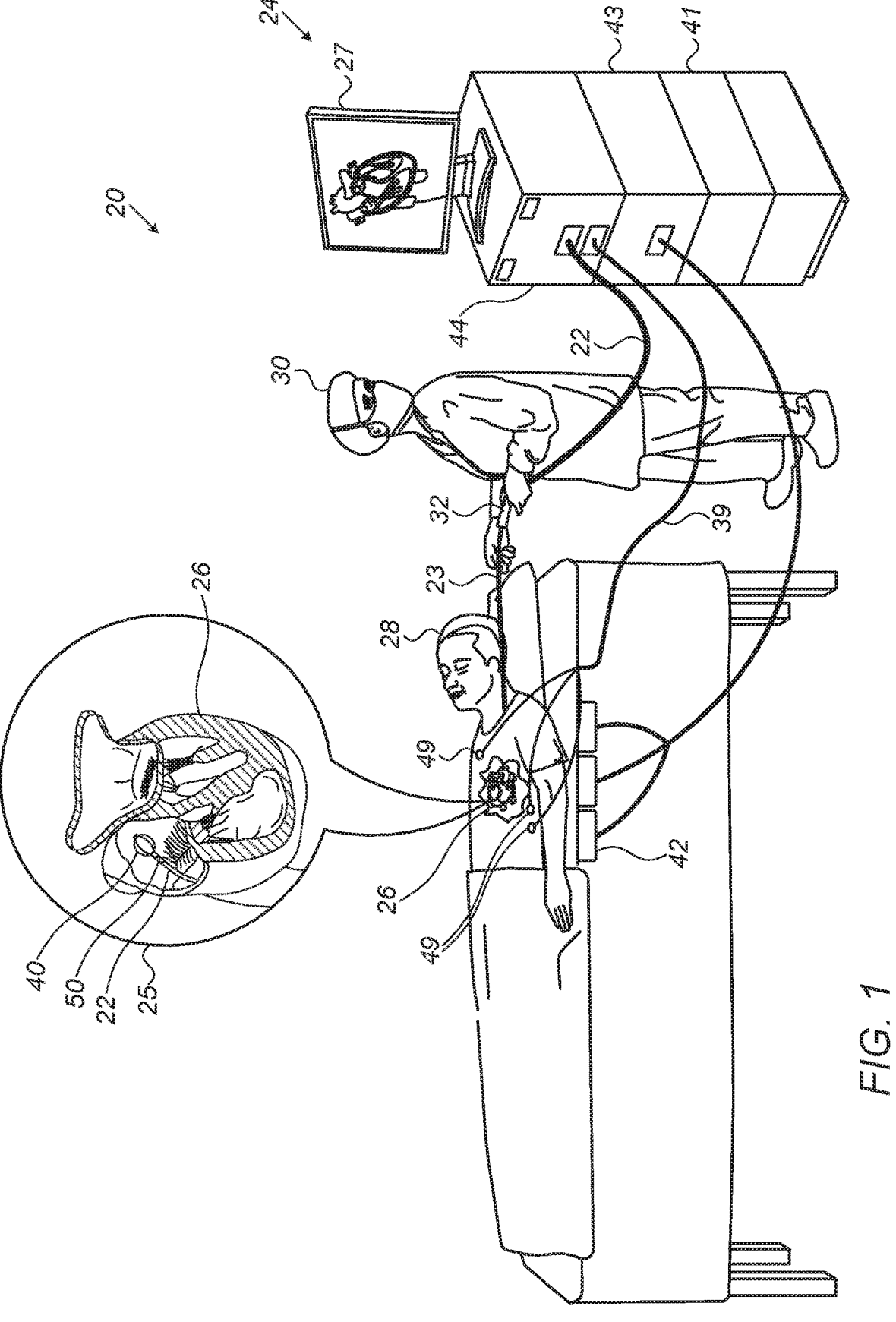
FIG. 1 is a schematic pictorial illustration of a catheter-based position tracking and ablation system that includes an Active Current Location (ACL) sub-system and a magnetic-sensing sub-system, in accordance with an embodiment of the present invention.

Embodiments of the present invention that are described hereinafter provide location tracking methods and systems that use position-indicative signals received from electrodes fitted at the distal end of an inflatable balloon catheter. The electrodes are disposed over and/or in proximity to the inflatable balloon.

In some embodiments, some of the electrodes are used for ablation and others for electrophysiological sensing. The positions of the various electrodes can be tracked based on electrical signals generated by the electrodes. These electrical position-indicative signals are measured relative to body surface electrodes attached to the patient's skin.

In some embodiments, the electrical position-tracking methods rely on sensing impedance signals, while in other embodiments the methods rely on sensing voltage signals. In another embodiment, the electrical position tracking methods rely on the proportions of distribution of currents, transmitted by the catheter electrodes and measured by the body surface electrodes (patches) attached to the patient's skin.

An example of a system applying currents distribution measurements is the Carto®3 system, which is made by Biosense-Webster (Irvine, California).

In the description hereinafter, the Carto®3 system serves as an example of an electrical signal-based position-tracking system. The Carto®3 system applies an Active Current Location (ACL) impedance-based position-tracking method. In some embodiments, using the above noted ACL method, a processor in the position-tracking system estimates the location and orientation of a balloon catheter.

In some embodiments, to visualize catheters which do not include a magnetic sensor, the processor applies an additional electrical signal-based method on top of ACL, referred to as the Independent Current Location (ICL) method. In the ICL method, the processor calculates a local scaling factor for each voxel of a volume of the balloon catheter. The factor is determined using a catheter with multiple electrodes having a known spatial relationship, such as a Lasso-shaped catheter. However, although yielding accurate local scaling (e.g., over several millimeters), ICL is less accurate when applied to a balloon catheter, whose size is on the order of centimeters. The position-signals generated by the ablation electrodes are typically too coarse to be useful on their own (e.g., they are spread in space due to the large area of ablation-electrodes).

In some embodiments of the disclosed invention, a processor uses first and second electrodes fitted on a shaft of the catheter, on either side of the balloon, to accurately scale the ICL measurements. The first and second electrodes, also named hereinafter "sensing-electrodes," are small-area electrodes, and thus produce localized position-signals that can be accurately processed by the processor to indicate an exact scaling factor. The distance between these two electrodes is both known and large, and therefore suitable to accurately scale (i.e., apply ICL to) current-based position calculations of a large structure such as a balloon.

Using two such electrodes, the disclosed ICL method provides an undistorted representation of a physical distribution in space of the various elements, such as of ablation electrodes. In some embodiments, based on the known distance and position-signals from the first and second electrodes, the processor scales positions of various elements disposed over the balloon catheter.

In some cases, using ACL and ICL methods may still not be accurate enough to determine an exact orientation of the balloon inside an organ (e.g., inside a cardiac chamber). The balloon orientation is defined as a direction in space to which the longitudinal axis of the distal end of the shaft points. As a result, an equator representing the orientation of the ablation electrodes may be tilted at some unknown angle, relative, for example, to an opening of a pulmonary vein to be ablated by the electrodes. The physician needs to know that orientation accurately enough in order to direct the balloon to correctly face the opening.

Thus, as a further improvement, in some embodiments the processor also uses magnetic position-tracking measurements of a position sensor coupled to the distal end of the catheter. This measurement is especially effective since it gives an accurate measure of the angular orientation of the catheter. The processor calculates the orientation and uses the information to further refine the estimated positions and the orientation of the ablation-electrodes.

In an embodiment, the processor runs in parallel the ACL calculations, the ICL calculations, and the magnetic direction calculations.

By combining the position and orientation tracking stages described above (i.e., ACL, ICL, and magnetic direction), embodiments of the present invention enable a physician operating the balloon catheter to a) collect anatomically accurate electrophysiological data using the catheter, and b) direct the balloon inside a cavity, such as a cardiac-chamber so as to, for example, uniformly ablate an ostium of a pulmonary vein inside the left atrium of the heart.

The disclosed technique may eliminate the need to incorporate additional means for tracking the balloon catheter position and orientation, and may therefore simplify balloon catheters, as well as the tracking and ablation systems operating them. For example, the disclosed technique may save fitting an additional position sensing element at the distal end of the balloon catheter, and the potential need for an additional sub-system to operate such an additional position-sensing element.

System Description

FIG. 1 is a schematic pictorial illustration of a catheter-based position tracking and ablation system 20 that includes an Active Current Location (ACL) sub-system and mag-netic-sensing sub-system, in accordance with an embodiment of the present invention. System 20 is used to determine the position of a balloon catheter 40, seen in an inset 25 fitted at a distal end of a shaft 22. Typically, balloon catheter 40 is used for therapeutic treatment, such as spatially ablating cardiac tissue, for example at the left atrium.

System 20 can determine the orientation of balloon catheter 40 (i.e., the direction in space as defined by the distal end of a shaft 22). For position and direction measurements, balloon catheter 40 incorporates a first and second sensing-electrodes fitted on shaft 22, on either side of the balloon (shown in FIG. 2) and a magnetic sensor 50, respectively. The first and second sensing-electrodes and magnetic sensor 50 are connected by wires running through shaft 22 to various driver circuitries in a console 24.

Physician 30 navigates balloon catheter 40 to a target location in a heart 26 of a patient 28 by manipulating shaft 22 using a manipulator 32 near the proximal end of the catheter and/or deflection from a sheath 23. Balloon catheter 40 is inserted, in a folded configuration, through sheath 23, and only after the balloon is retracted from the sheath 23 does balloon catheter 40 regain its intended functional shape. By containing balloon catheter 40 in a folded configuration, sheath 23 also serves to minimize vascular trauma on its way to the target location.

Console 24 comprises a processor 41, typically a general-purpose computer and a suitable front end and interface circuits 44 for receiving signals from ACL surface electrodes 49 (named hereinafter "ACL patches 49"), which are seen in the exemplified ACL system as attached by wires running through a cable 39 to the chest and to the back of patient 28.

In some embodiments, the processor uses the position-signals received from the various electrodes to estimate a position of the balloon catheter inside an organ, such as inside a cardiac chamber. In an embodiment, the processor correlates the position signals received from the electrodes with previously acquired magnetic location-calibrated position signals (i.e., using the ACL method), to estimate the balloon position inside a cardiac chamber.

The ICL method, in which positions are calculated based on current distribution proportions can have errors and may indicate of a distorted shape of the balloon catheter, due to the non-linear nature of the current-based ICL space. In some embodiments, processor 41 further applies the disclosed ICL method to scale the balloon catheter shape into a correct one, based on known smaller scale distances between electrodes of a lasso-shaped catheter, as well as based on larger scale distances, themselves based on the known distance between the first and second electrodes at the ends of the balloon.

In some embodiments, processor 41 accurately determines position coordinates of the first and second sensing-electrodes fitted at balloon catheter 40 inside heart 26. Processor 41 determines the position coordinates, which are based on, among other inputs, measured impedances, or on proportions of currents distribution, between the sensing-electrodes and ACL patches 49 (i.e., using ACL and ICL methods described above). Console 24 drives a display 27, which shows the distal end of the catheter position inside heart 26.

The method of electrode position sensing using system is implemented in various medical applications, for example in the CARTO™ system, produced by Biosense-Webster Inc. (Irvine, California) and is described in detail in U.S. Pat. Nos. 7,756,576, 7,869,865, and 7,848,787, whose disclosures are all incorporated herein by reference.

Console 24 further comprises a magnetic-sensing subsystem. Patient 28 is placed in a magnetic field generated by a pad containing magnetic field generator coils 42, which are driven by unit 43. The magnetic fields generated by coils 42 generate direction signals in a magnetic sensor 50, which are then provided as corresponding electrical inputs to processor 41, which uses these to calculate an orientation of balloon catheter 40, thus correcting the positions derived using the ACL and ICL methods.

The method of position sensing using external magnetic fields is implemented in various medical applications, for example, in the CARTO™ system, produced by Biosense Webster Inc., and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be applied for position-sensing and/or controlling ablation using many sorts of multi-electrode catheters, such as multi-arm catheters (e.g., Pentaray®, made by Biosense-Webster).

Scaling Impedance Location Measurements of a Balloon Catheter

Figure 2:
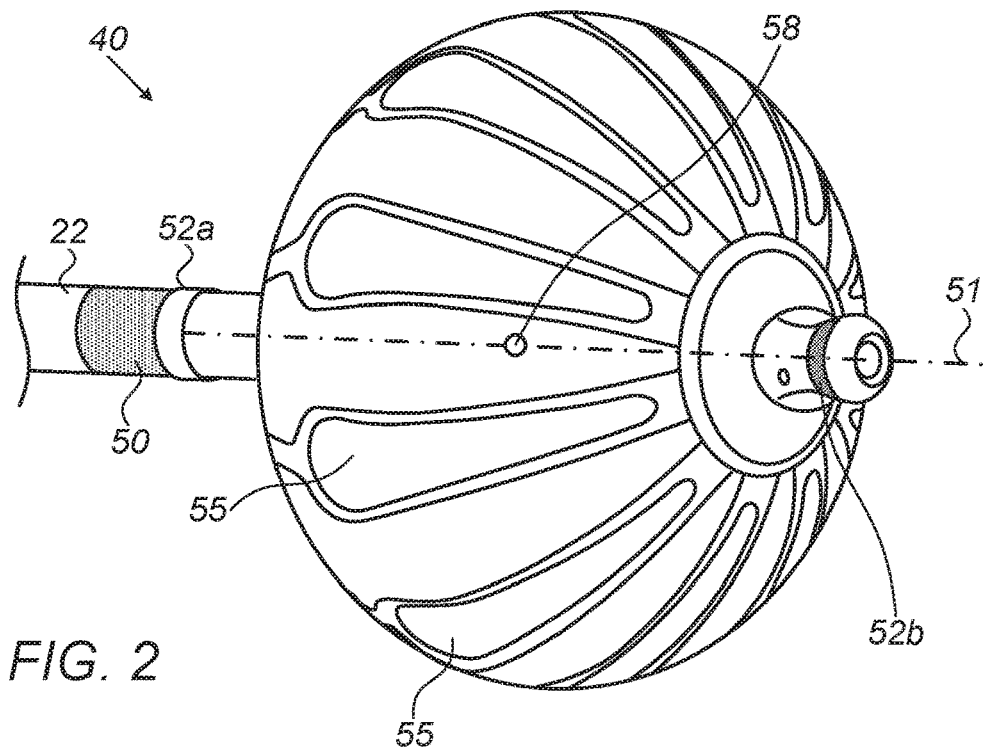
FIG. 2 is a schematic pictorial illustration of the balloon catheter of FIG. 1, in accordance with an embodiment of the present invention.

FIG. 2 is a schematic pictorial illustration of balloon catheter 40 of FIG. 1, in accordance with an embodiment of the present invention. As seen, balloon 40 is fitted at the distal end of shaft 22, which defines a longitudinal axis 51. Center point 58 on axis 51, which is the origin of the sphere shape of balloon 40, defines a nominal position of balloon 40. In the example shown in FIG. 2, the first and second sensing electrodes are denoted proximal-electrode 52a and distal-electrode 52b, respectively. As seen, the two sensing-electrodes are fitted on shaft 22, on either side of balloon 40. Additionally seen is a magnetic position sensor 50 fitted just proximally to proximal-electrode 52a. Also seen are ablation electrodes 55, which are disposed in a circumference over balloon 40, which occupy a large area as compared with sensing-electrodes 52a and 52b.

Typically, the disposed ablation electrodes are evenly distributed along the balloon's equator, where the equator is aligned perpendicular to the longitudinal axis of the distal end of shaft 22. In some embodiments, using the disclosed ICL scaling method, the ICL measured locations of electrodes 55 are scaled into, for example, correctly spaced locations over the equator.

In an optional embodiment, the processor applying ICL further improves the accuracy of the scaling factor, by additionally using the coarse position-signals that ablation-electrodes 55 generate.

The illustration shown in FIG. 2 is chosen purely for the sake of conceptual clarity. Other configurations of sensing-electrodes are possible. Additional functionalities may be included in magnetic sensor 50. Elements which are not relevant to the disclosed embodiments of the invention, such as irrigation ports, are omitted for the sake of clarity.

Figure 3:
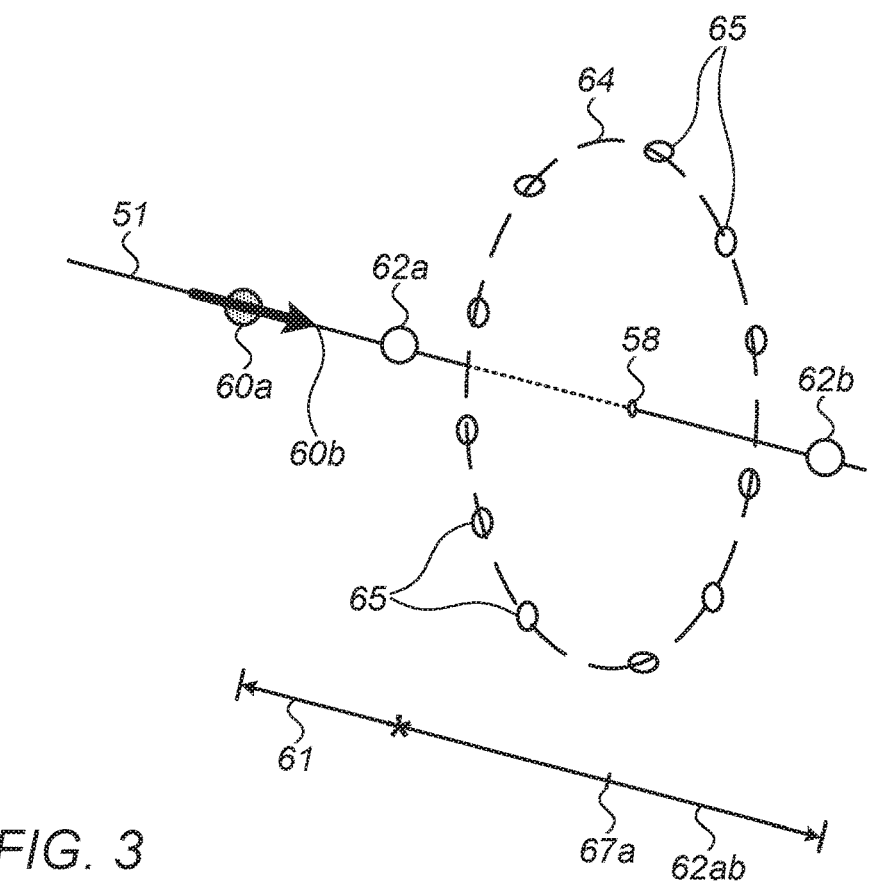
FIG. 3 is a schematic pictorial illustration of various datum points over the balloon catheter of FIG. 2, in accordance with an embodiment of the present invention.

FIG. 3 is a schematic pictorial illustration of various datum points over the balloon catheter of FIG. 2, in accordance with an embodiment of the present invention. The location of the datum points may be presented, for example, in a coordinate system defined for the electro-anatomical map stored in the processor, to which the system correlates the position in space of balloon 40.

Proximal-electrode 52a is located at a position 62a, while distal electrode 52b is located at a position 62b. Magnetic sensor 50 is located at a position 60a, while, as described above, sensor 50 is capable of indicating a direction 60b, which is parallel to the direction of shaft 22 (i.e., parallel to axis 51). Despite the large areas of ablation electrodes 55, a consistent and useful representation of the electrodes in space is possible, in the form of locations 65 on an equator 64 embedded in a plane orthogonal to axis 51. In other words, when the balloon is fully inflated, locations 65 lay on a circle having the maximal transverse diameter of balloon

40. A nominal position of balloon 40 is defined by center point 58, which is also the center of equator 64.

As seen in FIG. 3, distance 62*ab* is the known distance between proximal electrode 52*a* and distal electrode 52*b*. As seen, locations 65 lay in a plane that intersects axis 51 at point 67*a*, approximately in the middle of distance 62*ab*, between positions 62*a* and 62*b*. Thus, center position 67*a* is very close to the middle of distance 62*ab*. As will be shown below, using embodiments of the present invention, center position 67*a* and direction 60*b* of balloon 40, and the locations of its various elements, are measured while the balloon is inside a cardiac chamber.

Position 67*a* is estimated using position signals from the sensing-electrodes 52*a* and 52*b* that are processed with the ACL method. Direction 60*b* is estimated by the magnetic tracking sub-system using signals from magnetic sensor 50. Scaling of element positions, such as positions 65, is done by processing the position signals from the sensing-electrodes with the ICL method, together with the knowledge of the mechanical distances between electrodes, as elaborated below.

Figure 4:
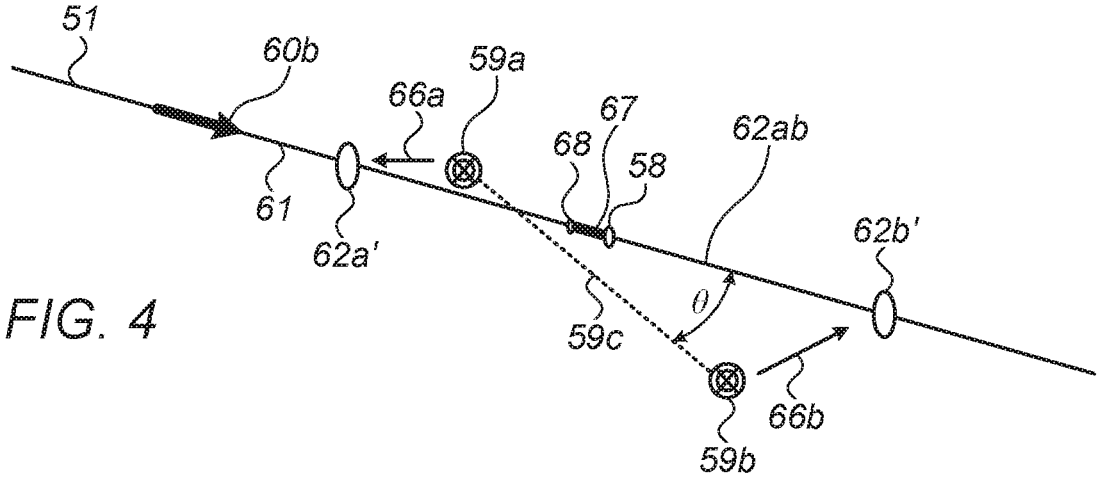
FIG. 4 is a schematic pictorial illustration of a method for scaling impedance-measured locations, in accordance with an embodiment of the present invention.

FIG. 4 is a schematic pictorial illustration of a method for scaling impedance-measured locations, in accordance with an embodiment of the present invention. FIG. 4 shows an ICL-method obtained locations 59*a* of proximal-electrode 52*a* and location 59*b* of distal-electrode 52*b*. The measured locations 59*a* and 59*b* are inaccurate, as compared to datum points 62*a* and 62*b* of FIG. 3, which causes the estimate of a direction 59*c* to be off by an angle $\theta$ from the actual one (which is direction 60*b*). Correspondingly, the calculated equator encompassed by electrode 55 is wrongly tilted by the angle $\theta$ relative to its correct direction. In addition, a distance 59*c* between sensing-electrodes 52*a* and 52*b* is also inaccurate, indicating that the measured locations of the electrodes over the equator are also off scale (e.g., the equator has a wrong radius). The errors described above hinder, for example, accurately correlating the location and orientation of ablation electrodes 55 with tissue locations mapped by an electro-anatomical map for the purpose of ablation, such as over a circumference of an ostium of a pulmonary vein.

In some embodiments, the processor derives direction 60*b* from signals provided by magnetic sensor 50. The processor calculates a mean location from measured locations 59*a* and 59*b*, and projects that mean location on direction 60*b* to obtain an estimated center location 68, based on the known distance between the sensing electrodes. Corrective-displacements 66*a* and 66*b* are calculated to scale measured positions of sensing-electrodes 52*a* and 52*b*. The corrective-displacements align the electrode locations along direction 60*b* and distance-scaled locations 62*a'* and 62*b'* to the correct distance 62*ab* between the two.

The resulting corrected electrode locations 62*a'* and 62*b'* may still have a slight parallel-shift along axis 51, relative to actual locations 62*a* and 62*b*, by an error 67 in the center position, i.e., center point 58, in the mean location estimated by the ICL method. Error 67 is thus defined by the error between actual nominal location 58 and an ACL estimated location 68. Error 67 in the ICL-estimated center-position is acceptable because the processor can estimate sufficiently accurate equatorial positions of electrode 55 (not shown), based on the disclosed ACL, ICL and magnetic direction stages, and thus, for example, correlate these positions accurately enough with an electro-anatomical map of tissue.

Figure 5:
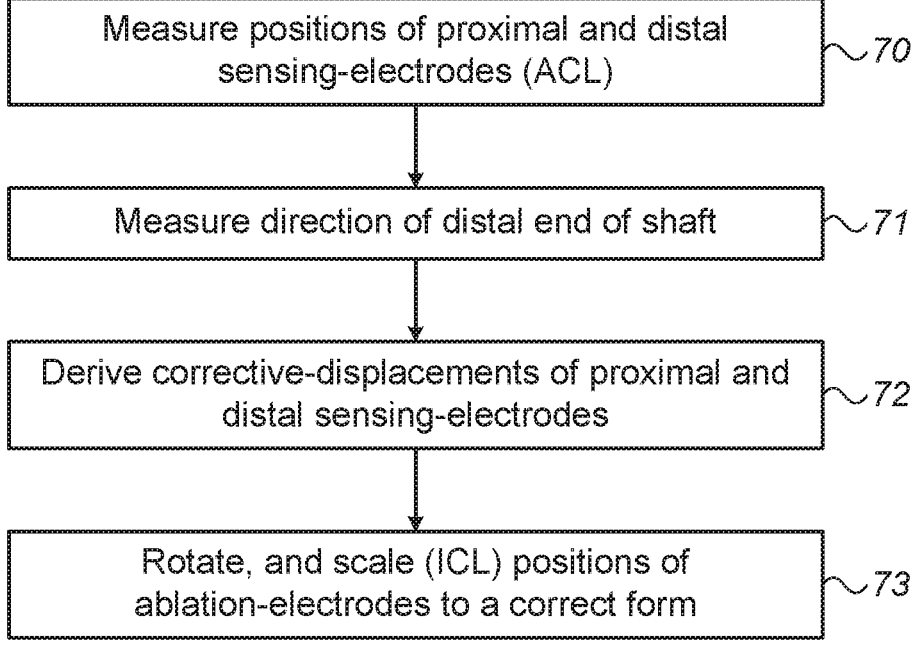
FIG. 5 is a flow chart that schematically illustrates a method for scaling impedance-measured locations, in accordance with an embodiment of the present invention.

FIG. 5 is a flow chart that schematically illustrates a method for scaling impedance-measured locations, in accordance with an embodiment of the present invention. The process begins with processor 41 calculating the nominal positions of electrodes 52*a* and 52*b*, using the ACL method, at an ACL positioning step 70. Next, processor 41 calculates direction 60*b*, based on signals from magnetic sensor 50, at a magnetic direction calculation step 71. At a calculation step 72, processor 41 derives corrective-displacements 66*a* and 66*b*, and uses the derived displacements, at a correction step 73, to rotate and to scale the positions of electrodes 55 to an equator of the correct balloon diameter within a plane perpendicular to correct direction 60*b*.

The example flow chart shown in FIG. 5 is chosen purely for the sake of conceptual clarity. In alternative embodiments, additional calculations may be applied. Additional steps may follow, such as correlating electrodes 55 positions with an electro-anatomical map.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
   a balloon catheter comprising a shaft, an inflatable balloon fitted at a distal end of the shaft, multiple large-area ablation electrodes disposed on the inflatable balloon, first and second small-area sensing electrodes fitted on the shaft, the first small-area sensing electrode proximal of the inflatable balloon and the second small-area sensing electrode distal of the inflatable balloon, and a magnetic sensor fitted on the shaft proximal of the first small-area sensing electrode; and
   a processor, which is configured to:
      receive position signals (i) generated as coarse position-signals by the multiple large-area ablation electrodes disposed on the inflatable balloon and (ii) from the first and second small-area sensing electrodes fitted on the shaft;
      receive from the magnetic sensor one or more direction signals indicative of a direction of the distal end, and
      calculate positions of the multiple large-area ablation electrodes disposed on the balloon based on the received signals of positions of (i) the multiple large-area ablation electrodes, and (ii) the first and second small-area sensing electrodes, on the one or more direction signals, and on a known distance between the first and second small-area sensing electrodes, by estimating positions of the first and second small-area sensing electrodes based on the position signals;
         estimating a direction of the catheter distal end based on the one or more direction signals;
         based on the known distance between the first and second small-area sensing electrodes, calculating displacements of the first and second small-area sensing electrodes such that the first and second small-area sensing electrodes are brought into correct positions along the direction of the catheter distal end; and
scaling the positions of the multiple large-area ablation electrodes based on the calculated displacements.

2. A method, comprising:
generating electrical excitation energy around a patient's organ;
generating a magnetic field around a patient's organ; and
in a processor,
receiving position signals generated by multiple large-area ablation electrodes in response to the electrical excitation energy, the multiple large-area ablation electrodes disposed on an inflated balloon fitted at a distal end of a catheter;
receiving additional position signals generated by first and second small-area sensing electrodes in response to the electrical excitation energy, the first and second small-area sensing electrodes fitted on a shaft of the catheter, the first small-area sensing electrode being proximal of the balloon, the second small-area sensing electrode being distal of the balloon;
based on the position signals and the additional position signals, determining positions of the multiple large-area ablation electrodes in a coordinate system that includes the patient's organ, by;
receiving a direction signal generated by a magnetic sensor in response to the magnetic field, the magnetic sensor fitted on the shaft and proximal of the first small-area sensing electrode, the direction signal representative of a direction to which a distal end of the shaft points; and
applying corrective displacements, including adjusting the direction of the distal end of the shaft in the coordinate system based on the direction signal and adjusting the positions of the multiple large-area ablation electrodes in the coordinate system based on a scaling factor.

3. The method of claim 2, wherein the positions of the multiple large-area ablation electrodes include positions of the multiple large-area ablation electrodes on an equator in the coordinate system, the equator defined by a radius representative of the inflated balloon, and the adjusting the positions of the multiple large-area ablation electrodes includes adjusting the positions of the multiple large-area ablation electrodes on the equator.

4. The method of claim 3, wherein the adjusting the positions of the multiple large-area ablation electrodes on the equator includes adjusting the radius of the equator in the coordinate system.

5. The method of claim 3, wherein the adjusting the radius of the equator includes:
determining a mean location based on the additional position signals of the first and second small-area sensing electrodes; and
projecting the mean location onto the direction of the distal end of the shaft to determine an estimated center of the balloon.

6. The method of claim 2, wherein the determining the positions of the multiple large-area ablation electrodes is based on previously acquired magnetic location-calibrated position signals.

7. The method of claim 2, wherein the scaling factor is based on position signals of the first and second small-area sensing electrodes acquired by current distribution proportions.

8. The method of claim 2, wherein the scaling factor is based on a known distance between the first and second small-area sensing electrodes.

9. The method of claim 2, further including adjusting the scaling factor by using coarse position-signals generated by the multiple large-area ablation electrodes in response to the electrical excitation energy.

10. The method of claim 2, wherein the determining the positions of the multiple large-area ablation electrodes includes determining in parallel positions of the first and second small-area sensing electrodes, the direction of the distal end of the shaft, and the corrective displacements.

11. A system, comprising:
a balloon catheter comprising:
a shaft,
an inflatable balloon fitted at a distal end of the shaft,
multiple large-area ablation electrodes disposed on the inflatable balloon,
first and second small-area sensing electrodes fitted on the shaft, the first small-area sensing electrode proximal of the inflatable balloon, the second small-area sensing electrode distal of the inflatable balloon, and
a magnetic sensor fitted on the shaft, proximal of the first small-area sensing electrode;
a processor configured to:
receive position signals generated by the multiple large-area ablation electrodes in response to electrical excitation energy;
receive additional position signals generated by the first and second small-area sensing electrodes in response to the electrical excitation energy;
based on the position signals and the additional position signals, determine positions of the multiple large-area ablation electrodes within a coordinate system that includes a patient's organ, by;
receiving a direction signal generated by the magnetic sensor, the direction signal representative of a direction to which a distal end of the shaft points; and
applying corrective displacements, including adjusting the direction of the distal end of the shaft in the coordinate system based on the direction signal and adjusting the positions of the multiple large-area ablation electrodes in the coordinate system based on a scaling factor.

12. The system of claim 11, wherein the positions of the multiple large-area ablation electrodes include positions of the multiple large-area ablation electrodes on an equator in the coordinate system, the equator defined by a radius representative of the inflated balloon, and the processor is configured to adjust the positions of the multiple large-area ablation electrodes by adjusting the positions of the multiple large-area ablation electrodes on the equator.

13. The system of claim 12, wherein the processor is configured to adjust the positions of the multiple large-area ablation electrodes on the equator by adjusting the radius of the equator in the coordinate system.

14. The system of claim 12, wherein the processor is configured to adjust the radius of the equator by:
determining a mean location based on the additional position signals of the first and second small-area sensing electrodes; and
projecting the mean location onto the direction of the distal end of the shaft to determine an estimated center of the balloon.

15. The system of claim 11, wherein the processor is configured to determine the positions of the multiple large-area ablation electrodes based on previously acquired magnetic location-calibrated position signals.

16. The system of claim 11, wherein the processor is configured to determine the positions of the first and second small-area sensing electrodes based on current distribution proportions.

17. The system method of claim 11, wherein the processor is configured to determine the scaling factor based on a known distance between the first and second small-area sensing electrodes.

18. The system of claim 11, wherein the processor is configured to adjust the scaling factor by using coarse position-signals generated by the multiple large-area ablation electrodes in response to the electrical excitation energy.

19. The method of claim 11, wherein the processor is configured to determine the positions of the multiple large-area ablation electrodes by determining in parallel positions of the first and second small-area sensing electrodes, the direction of the distal end of the shaft, and the corrective displacements.

* * * * *